(12) United States Patent
Kunz et al.

(10) Patent No.: US 10,827,907 B2
(45) Date of Patent: Nov. 10, 2020

(54) TROCAR SYSTEM

(76) Inventors: Reiner Kunz, Kleinmachnow (DE);
Michael Schmidt, Halifax (CA)

(*) Notice: Subject to any disclaimer, the term of this patent is extended or adjusted under 35 U.S.C. 154(b) by 0 days.

(21) Appl. No.: 13/990,289

(22) PCT Filed: Nov. 29, 2011

(86) PCT No.: PCT/EP2011/071222
§ 371 (c)(1),
(2), (4) Date: May 29, 2013

(87) PCT Pub. No.: WO2012/072602
PCT Pub. Date: Jun. 7, 2012

(65) Prior Publication Data
US 2013/0245374 A1 Sep. 19, 2013

(30) Foreign Application Priority Data
Nov. 29, 2010 (DE) .................. 10 2010 060 877

(51) Int. Cl.
*A61B 1/00* (2006.01)
*A61B 17/34* (2006.01)
(Continued)

(52) U.S. Cl.
CPC ............ *A61B 1/00045* (2013.01); *A61B 1/05* (2013.01); *A61B 1/06* (2013.01); *A61B 17/3417* (2013.01);
(Continued)

(58) Field of Classification Search
CPC .. A61B 1/05; A61B 1/055; A61B 1/06; A61B 1/07; A61B 1/0661; A61B 1/00025;
(Continued)

(56) References Cited

U.S. PATENT DOCUMENTS 5,271,380 A  12/1993  Riek et al.
5,392,067 A   2/1995  Konno et al.
(Continued)

FOREIGN PATENT DOCUMENTS

DE      4035146 C2   5/1992
DE     19547246 C1   3/1997
(Continued)

OTHER PUBLICATIONS

International Preliminary Report on Patentability, dated Jun. 4, 2013, corresponding to PCT/EP2011/071222; with English translation.
(Continued)

*Primary Examiner* — Timothy J Neal
*Assistant Examiner* — William B Chou
(74) *Attorney, Agent, or Firm* — Ladas & Parry, LLP; Malcolm J. MacDonald

(57) ABSTRACT

The invention relates to a trocar system for a minimally invasive work station, comprising an endoscopic instrument (2) having imaging means (3) and a device for transmitting the signals containing the image information to a display unit (6) and, as required, work tools, further comprising a trocar assembly (7 to 16) having a trocar sleeve, which is designed to receive a pin, including imaging means (8, 14), provided with a tip that is permeable to imaging media having different wavelengths, wherein the imaging means are provided to make the work field visible through the distal end of the pin and a device (16) is provided for transmitting the signals containing the image information to a display unit (6). The trocar assembly (7 to 16) and the minimally invasive instrument (3) are provided for separate use and for displaying the respective image information for the same display unit (6). The pin is provided with an on/off switch (13). The display device is equipped to display the image
(Continued)

Figure 1:
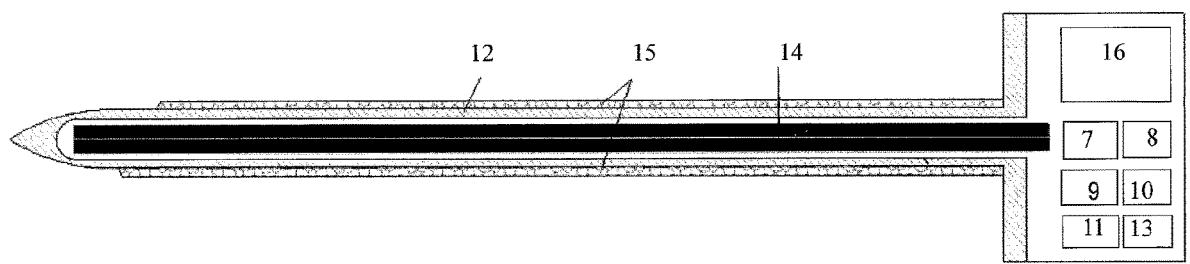

information transmitted by the pin when the pin is switched on and to suppress the display of the image information transmitted by the endoscopic instrument, and to display the information transmitted by the endoscopic instrument when the pin is switched off.

17 Claims, 2 Drawing Sheets

(51) Int. Cl.
   *A61B 1/05* (2006.01)
   *A61B 1/06* (2006.01)
   *A61B 90/00* (2016.01)
(52) U.S. Cl.
   CPC ..... *A61B 90/361* (2016.02); *A61B 2017/3454* (2013.01)
(58) Field of Classification Search
   CPC ............ A61B 1/00027; A61B 1/00032; A61B 1/00043; A61B 1/00055; A61B 1/00045; A61B 1/0005; A61B 1/00052
   USPC ........ 600/102, 103, 109, 110, 112, 113, 114, 600/117, 160
   See application file for complete search history.

(56) References Cited

U.S. PATENT DOCUMENTS

| | | | |
|---|---|---|---|
| 5,431,151 | A | 7/1995 | Riek et al. |
| 5,685,820 | A | 11/1997 | Riek et al. |
| 5,686,820 | A | 11/1997 | Riggio, Jr. |
| 5,817,061 | A | 10/1998 | Goodwin et al. |
| 6,001,084 | A | 12/1999 | Riek et al. |
| 6,007,481 | A | 12/1999 | Riek et al. |
| 6,717,609 | B2 | 4/2004 | Sugimoto et al. |
| 2002/0047897 | A1 | 4/2002 | Sugimoto |
| 2004/0080612 | A1 | 4/2004 | Sugimoto |
| 2007/0255100 | A1* | 11/2007 | Barlow ................ A61B 1/0005 600/114 |
| 2008/0033450 | A1 | 2/2008 | Bayer et al. |
| 2008/0243162 | A1 | 10/2008 | Shibata et al. |
| 2009/0192390 | A1 | 7/2009 | Berguer et al. |
| 2011/0069278 | A1 | 3/2011 | Gueder |

FOREIGN PATENT DOCUMENTS

| | | |
|---|---|---|
| DE | 19850224 A1 | 10/1998 |
| DE | 10062631 A1 | 6/2001 |
| DE | 10101064 A1 | 7/2001 |
| DE | 69330169 T2 | 9/2001 |
| DE | 10110427 A1 | 9/2002 |
| DE | 10345640 A1 | 4/2005 |
| DE | 10333956 B4 | 11/2005 |
| DE | 102006051736 A1 | 5/2008 |
| DE | 102010060877 A1 | 5/2012 |
| EP | 0177177 A2 | 4/1986 |
| EP | 0726784 B1 | 4/2001 |
| JP | S61085934 A | 5/1986 |
| JP | 05103758 A | 4/1993 |
| JP | H07265264 A | 10/1995 |
| JP | H8503401 A | 4/1996 |
| JP | 1014926 A | 1/1998 |
| JP | 2000116599 A | 4/2000 |
| JP | 2001037719 A | 2/2001 |
| JP | 2001258835 A | 9/2001 |
| JP | 2003265402 A | 9/2003 |
| JP | 2009106360 A | 5/2009 |
| JP | 2009219612 A | 10/2009 |
| JP | 2010512959 A | 4/2010 |
| JP | 2010268328 A | 11/2010 |
| WO | 9411040 | 5/1994 |
| WO | 9426167 | 11/1994 |
| WO | 2000/24317 A1 | 5/2000 |
| WO | 03021329 A2 | 3/2003 |
| WO | 20051032632 A1 | 4/2005 |
| WO | 20071070641 A2 | 6/2007 |
| WO | 2010050243 A | 5/2010 |
| WO | 2010097315 A1 | 9/2010 |
| WO | 20121072602 A1 | 6/2012 |

OTHER PUBLICATIONS

Japanese Office Action dated Dec. 9, 2014, corresponding to Japanese Patent Application No. 2013-540413.

* cited by examiner

TROCAR SYSTEM

This application is a 371 of PCT/EP2011/071222, filed on Nov. 29, 2011, which is incorporated herein by reference.

The invention relates to a trocar arrangement, with the aid of which access to a body cavity or body structure can be created by sharp or blunt penetration and the access can be held open by a tube (for example, a sleeve, a tube, working channel, hose). It is a shaft which is located in a tube and the point of which closes the opening of the tube. The shaft is provided with imaging means to make the working field visible. A trocar arrangement such as this makes it possible for the outer sleeve to be carried along even with the first application step and to remain in position.

Minimally invasive surgical procedures in which, for example, a trocar arrangement of the type mentioned in the introduction creates an opening, have recently become very common in diagnostics and treatment. With the aid thereof, access can be gained to preformed body cavities or body structures such as the thorax, trachea, ventricles of the brain, abdomen, renal pelvis, bladder, uterus, amniotic sack or intervertebral disc, but also to vessels or defined tissue layers of the body. During such surgery, the initial access is the most difficult and is the most dangerous part for the patient. Various techniques have been developed to enable reliable monitoring of the puncture procedure.

Thus Veress needles are used blind or with the aid of integrated optics for puncturing purposes (see for example DE 195 47 246 C1). The use of a trocar instrument only to penetrate body tissue has also become known (see U.S. Pat. No. 5,685,820 A).

A laparoscopic instrument in accordance with U.S. Pat. No. 5,817,061 A or DE 693 30 169 T2 is fitted with fibre optic means, electrical coupling means and a video camera. The video images are displayed on a video monitor so that the surgeon can monitor the advancement of the tip of the instrument with the aid of the monitor.

Many minimally invasive surgical procedures are carried out using 30° or 45° optics, whereas it is expedient that the puncture procedure is visually monitored using 0° optics. During routine operation this means that second sterile optics with a different angular field must be docked-on or a second video camera with second optics must be provided from the outset. Assisting personnel must swap over the connections, for example, of the video camera, and this can lead to a tangle of cables and disrupt the progress of the surgery.

Since, depending on the surgery to be carried out, different endoscopes, arthroscopes, etc are used, requiring different levels of light and differing in terms of the size of the image generated, etc, the camera settings must be determined at the beginning of surgery or when a different endoscopic instrument is used. This is usually time-consuming and difficult to carry out. WO 2007/070641 A2 describes that the imaging data—which are dependent on physical properties of an endoscope—of a camera coupled to an endoscope are used automatically to identify the type of endoscope. Parameters, processing or display of camera images are then selected.

For imaging purposes, it is also possible to refrain from using visible light. Thus the Stryker Corporation has developed a laparoscope in which infrared light is used for imaging, being able to penetrate up to 12 mm of tissue but without heating the tissue. For example, the use of a puncture technique with ultrasound guidance is known from DE 198 50 224 A1.

DE 103 33 956 B4 discloses a viewing obturator with a tube through which optics corresponding to endoscopes and provided with an optical shaft and a transparent penetrating tip extend. The penetrating tip protrudes out of the distal end of the tube. After insertion into the body cavity the tube remains in the body orifice and the optical shaft and penetrating tip are then withdrawn. The optical shaft is then re-introduced and, by means of its working channel, instruments, flushing liquids, etc are passed through in order to be able to monitor examinations and operations as they are being carried out.

To allow patients to breathe, the intubation tube is normally introduced via the oral cavity through the glottis into the airway of the patient, wherein auxiliary optical means are used to monitor the intubation process. In the case of such an intubation device in accordance with DE 101 10 427 A1 a tube with a guide wire as a guidance aid is used, optics with a video chip being attached at its tip. The image can be transmitted to a monitor via a cable or radio.

If the intubation of a patient through the glottis is not possible, a tracheotomy or cricothyrotomy must be performed and the intubation tube then passed through this access point. Visual monitoring of the puncture process is in many cases carried out by endotracheal insertion of fibre optics (bronchoscope).

DE 103 45 640 A1 describes a puncturing tracheotomy device operating according to the Seldinger technique, in which the tracheal cannula is provided with a guidance aid having a light source. An expanding body is placed onto the guidance aid. By means of a detector, the position of the guidance aid can be monitored visually and also electronically. Owing to the circumstances of the surgical operation in such a case, two guidance aids and optics etc are used in succession, which makes reconnection of equipment by assisting personnel necessary and makes working in the prevailing emergency situation more difficult.

The object of the invention is to create a trocar arrangement which permits easy operation, activation and display of imaging information.

This object is achieved in accordance with the invention in the case of a trocar system having the features of claim 1. Advantageous developments of the trocar system are stated in the dependent claims.

A trocar system for minimally invasive or endoscopic instruments in accordance with the invention for a working location is provided with a minimally invasive instrument having imaging means and a device for transmitting the signals containing the imaging information to a display device and, if necessary, working tools. A trocar arrangement with a trocar sleeve is provided, which is provided to receive a shaft, provided with a tip, including imaging means, wherein the distal end of the shaft is permeable for the respective imaging medium (light, ultrasound), the imaging means are provided to render the working field visible through the distal end of the shaft, and a device is provided for transmitting the signals containing the imaging information to a display device. The trocar arrangement and the minimally invasive instrument are provided for single use and to display their respective imaging information for the same display device. The imaging means and the transmission device or parts thereof are inserted, preferably in an encapsulated manner, in the distal end of the shaft or in the proximal end thereof. The shaft is provided with an on/off switch. The display device is arranged in such a way that it displays the imaging information transmitted from the shaft when the shaft is in the switched-on state, and suppresses the display of the imaging information transmitted from the endoscopic instrument, and it displays imaging information transmitted from the endoscopic instrument when the shaft is in the switched-off state.

The trocar system in accordance with the invention permits a simplified and secure technique requiring less input from personnel for initial access in minimally invasive diagnostics and treatment. Owing to them being difficult to sterilise, the elements are preferably inserted in an encapsulated manner into the obturator or shaft or its proximal end. This makes it possible to use them in obturators or guidance aids of different lengths and with different diameters.

The information signal transmitted from the trocar arrangement is preferably displayed on the display, usually monitors, as long as the light source and detector unit of the obturator are switched on. Switching on/off is effected via a switch on the proximal end, which is operated in a sterile manner by the person carrying out the examination. Less preferable is a corresponding switch on a unit located lower down, which contains, for example, the control unit, memory, etc because then there is a problem of lack of asepsis and disturbance to the concentration of the person carrying out the examination. Alternatively provision can be made for the trocar arrangement to be activated (contact switch) during introduction of the shaft or obturator into or through the outer sleeve (trocar, tube, stent). The operator can then select and activate the light source, detector units for different wavelengths and examination techniques. By forming the trocar arrangement in this way, the operator, i.e. the person carrying out the examination, is independent, even in the sterile working area, of the help of medical assistance personnel in selecting, activating and switching over the examination means and the display on the monitors. Furthermore, other people can also follow the individual steps of the initial access on site or at a physically remote location. The images of the trocar arrangement can be stored on a recording medium, for example, a central memory.

Provision can also be made to provide an eye-tracking device to actuate the shaft and its components or for switchover purposes. A design such as this also makes possible sterile switching over to the trocar arrangement and operation without further assisting staff.

After switching off the information transmission units located in the shaft or obturator, it is possible automatically to observe the information signal, in general the video image of the minimally invasive or endoscopic instrument used for the actual surgery, on monitors as the respective examination or treatment progresses, the depiction of which was previously suppressed by activation of the trocar unit.

With the arrangement in accordance with the invention, it is easier or unnecessary to change the optics, display technology (light, infrared, ultrasound-foetal pulse detection), the video chain etc. It is possible to use visible and invisible light as well as ultrasound at the respectively desired or necessary wavelengths. A number of communication problems, risk to the sterile working area, the necessity of assisting personnel being present, unnecessary cable tangles in the sterile working area, etc no longer occur.

The shaft is expediently a rod-shaped puncturing or guide duct. However, other designs are also possible depending on the individual application.

In one embodiment of the trocar arrangement in accordance with the invention, the imaging means are optical, wherein the light wavelength lies in the range of visible or invisible light (for example, infrared). The imaging means can additionally or alternatively also operate by ultrasound. The light source and/or light detector unit can be provided outside the shaft. The power source, detector and transmitter for different wavelengths required for imaging are disposed in parallel if appropriate. If the light source is not located at the distal end of the shaft or obturator, the latter contains an optical transmission unit (for example, light conductor) for sending light from the light source to the distal end and/or from the distal end to the light detector unit. The latter can be provided at the proximal end of the shaft. The optical transmission unit can include—apart from light conductors—video optics or, for example, a Hopkins rod lens system. The power source, detector unit and transmitter for different wavelengths required for imaging are disposed in parallel if appropriate.

The video optics expediently comprise illumination devices and, at the distal end, an image converter. A video chain is then provided for connection to a video camera.

A transmission unit for transmitting the imaging information to the central and/or display unit, and display device equipment are preferably provided in the shaft. This makes it possible also to fit out the proximal part of the trocar arrangement without the use of cables. The antenna for transmitters and receivers of the transmission unit is, for example, of the WLAN type. The display can then even be provided on a notebook in the case of a mobile solution.

A power supply unit for the imaging means is expediently provided in the shaft or at the proximal end thereof. This can be, in particular, a battery, an accumulator or a battery unit or accumulator unit. In an advantageous embodiment of the power supply unit a charge display or a warning device is provided which emits a signal indicating insufficient charge level in the battery (unit) or accumulator (unit). The power supply unit can be charged, for example, by external input of electromagnetic radiation so that the asepsis of the arrangement is not compromised by connection to charging equipment or the changing of batteries etc.

The trocar system and the trocar control system are suitable for all minimally invasive surgery but also for tracheotomies. The shaft can thus be an optical guide rod for the tracheotomy or cricothyrotomy, wherein a dilator such as, for example, a dilating trocar sleeve and an intubation tube are placed onto the guide rod. Furthermore, the shaft can be used as a guide rod during intubation to show the glottis.

Figure 2:
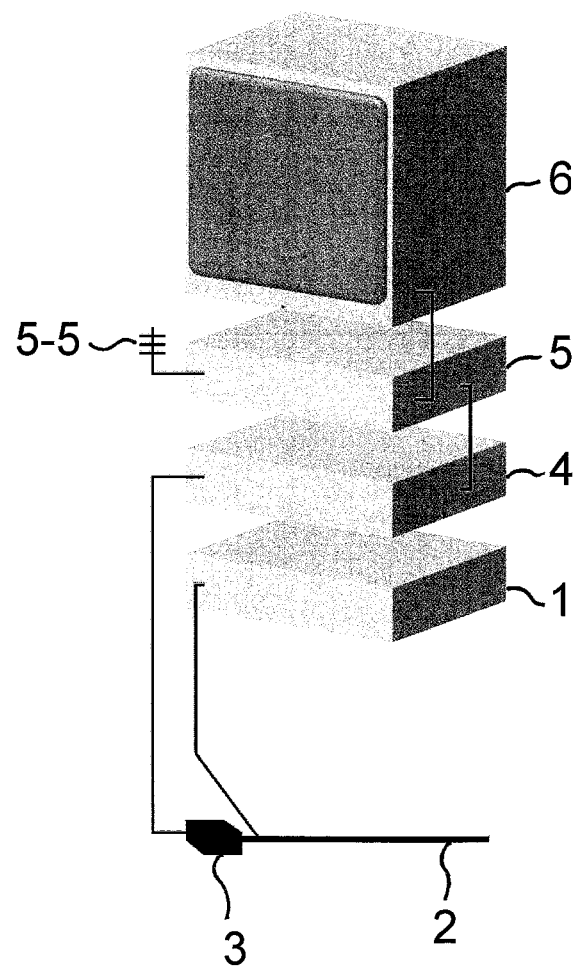

The invention is described further hereinunder with the aid of an exemplified embodiment and the drawing. This illustration serves only for the purposes of exemplification and is not intended to limit the invention to the feature combinations specifically mentioned. In the drawings:

FIG. 1 illustrates a schematic diagram showing the principle of a trocar arrangement in accordance with the invention and FIG. 2 illustrates a schematic diagram showing the principle of a video tower provided for conventional endoscopy and modified for use of the trocar arrangement in accordance with the invention.

FIG. 1 schematically shows a shaft or an obturator unit of a trocar arrangement in accordance with the invention. The shaft is for conventional puncturing purposes and is constructed and dimensioned accordingly.

A light conductor 14 extends through a duct 12 located in a sleeve 15 and from this light conductor visible or invisible light radiates out through the tip (or correspondingly transparent front end) of the duct 12 into the region under investigation, this tip being permeable for the corresponding wavelengths. A corresponding light source 7 for visible light is located at the proximal end of the trocar arrangement and conducts light into the light conductor 14. Also shown is a source 9 for light in the invisible wavelength range in the distal end of the duct 12, from which imaging information is transmitted via a transmission device, not shown, to the proximal end of the trocar arrangement. At this location is a respective decoder unit 8, 10 for visible and invisible (for example, infrared) light, which are used depending upon the wavelength of the light emitted from the light source (for example, cold light source). The wavelength used is dependent on the nature and location of the area under investigation. If this is essentially fixed, it is possible to dispense with the unnecessary decoder unit. An image converter with appropriate optics is preferably used.

Instead of light, ultrasound can also be used to produce the image, wherein ultrasound transmitters and receivers and the transmission device are designed and disposed appropriately.

A transmission unit 16 with an antenna is coupled to the decoder unit 8, 10 and transmits the imaging information signals to a display unit, i.e. the monitor 6 of a video tower illustrated in FIG. 2. Alternatively, a cable connection can also be used, wherein wireless transmission is preferred. The imaging information signals can also be input in parallel into a memory, not shown.

In the proximal end of the trocar arrangement there is also a power supply unit 11. This supplies, for example, the light source 7, the light decoder 8 and the transmission unit 16.

Furthermore, an on/off switch 13 is disposed at the proximal end of the trocar arrangement and by means thereof the trocar arrangement or the components of the trocar arrangement are switched on and off directly by the operator. A preferred representation of the imaging information signals on the monitor 6 is coupled thereto, while the information depicted in a standard form from an endoscope 2, for example, bronchoscope, is suppressed. In the case of a cricothyrotomy, a simple switch-over from the endoscope to the trocar makes switch-over hand movements and measures during this change between equipment or instruments unnecessary, which will save time which is urgently required in an emergency.

The above-mentioned video tower shown in FIG. 2 includes a receiver 5, provided with an antenna 5-5, from which the imaging information signals of the shaft are sent to the monitor 6 as long as this monitor is switched on.

If the trocar arrangement is not switched on, no signals are transmitted from it to the video tower and the video tower is then in the normal operating mode in which it displays the imaging information signals delivered from the endoscope 2 and generated by the light source 1, video camera 3 and video chain. These video signals are sent via a decoder 4 to the receiver 5, from which they are displayed on the monitor 6.

The invention claimed is:

1. In combination, a minimally invasive instrument and a trocar arrangement used together in a minimally invasive working location,
    wherein the minimally invasive instrument comprises:
    a first imaging means, and
    a device for transmitting signals containing imaging information to a display device, and
    wherein the trocar arrangement comprises:
    a sleeve,
    a shaft disposed in the sleeve, and
    a second imaging means disposed in the shaft,
    wherein a distal end of the shaft is transparent for the imaging,
    wherein the second imaging means renders a working field visible through the distal end of the shaft, and a device is provided for transmitting the signals containing imaging information to the display device,
    wherein the trocar arrangement and the minimally invasive instrument are provided for single use, and the display device is provided for displaying, alternatively, the imaging information of the minimally invasive instrument or the imaging information of the trocar arrangement,
    wherein the second imaging means and the device for transmitting the signals containing the imaging information, or parts of said second imaging means, and said device for transmitting the signals containing the imaging information to the display device, are positioned in the shaft, or in the proximal end thereof,
    wherein the shaft is provided with a switch,
    wherein the display device is configured to display the imaging information transmitted from the shaft,
    wherein the display device is configured to suppress the display of the imaging information transmitted from the minimally invasive instrument when the switch of the shaft is in a switched-on state, and
    wherein the display device displays imaging information transmitted from the minimally invasive instrument when the switch is in a switched-off state.

2. The trocar system according to claim 1, wherein at least one of the second imaging means and the device for transmitting the signals containing the imaging information to the display device is encapsulated.

3. The trocar system according to claim 1, wherein the switch is a contact switch.

4. The trocar system according to claim 3, wherein the sleeve is an outer sleeve.

5. The trocar system according to claim 1, wherein the shaft is rod-shaped.

6. The trocar system according to claim 1, wherein the second imaging means is at least one of an optical imaging means and an ultrasound imaging means.

7. The trocar system according to claim 6, wherein at least one of a light source and a light detector unit is disposed outside the shaft, and an optical transmission unit is disposed in the shaft.

8. The trocar system according to claim 7, wherein the optical transmission unit comprises a member selected from the group consisting of a light conductor, a video optics system, and a Hopkins rod lens system.

9. The trocar system according to claim 8, wherein the video optics system comprises an illumination device, an imaging sensor, and a video chain connectable to a video camera.

10. The trocar system according to claim 1, wherein the shaft comprises a transmission unit for transmitting the imaging information to at least one of a central unit and a display unit.

11. The trocar system according to claim 1, comprising a power supply unit for the second imaging means, the power supply unit being disposed in the shaft, or at a proximal end of the shaft.

12. The trocar system according to claim 11, wherein the power supply unit is selected from the group consisting of a battery, an accumulator, a battery unit, and an accumulator unit.

13. The trocar system according to claim 12, wherein the power supply unit comprises a charge display, or a warning device which emits a signal indicating insufficient charge level in the battery, the battery unit, the accumulator, or the accumulator unit.

14. The trocar system according to claim 11, wherein the power supply unit is chargeable by an external input of electromagnetic radiation.

15. The trocar system according to claim 1, wherein the shaft is an optical guide rod for a tracheotomy or cricothyrotomy, and a dilating trocar sleeve and an intubation tube are placed onto a guide rod.

16. The trocar system according to claim 1, further comprising an eye-tracking device to actuate the shaft and components of the shaft, or for switch-over purposes.

17. The trocar system according to claim 1, wherein the signals containing imaging information are transmitted to working equipment.

* * * * *